(12) United States Patent
Wiederin

(10) Patent No.: US 7,861,607 B1
(45) Date of Patent: Jan. 4, 2011

(54) PRESSURIZED FLUID STATION

(75) Inventor: Daniel R. Wiederin, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 515 days.

(21) Appl. No.: 11/590,310

(22) Filed: Oct. 31, 2006

(51) Int. Cl.
*B01L 3/02* (2006.01)
(52) U.S. Cl. .................................. 73/864.25
(58) Field of Classification Search ........................ None
See application file for complete search history.

(56) References Cited

U.S. PATENT DOCUMENTS

| | | | | |
|---|---|---|---|---|
| 3,604,267 A * | 9/1971 | Johns | ....................... | 73/864.82 |
| 3,960,020 A * | 6/1976 | Gordon et al. | ........... | 73/864.22 |
| 4,390,157 A * | 6/1983 | Meckstroth | .............. | 251/30.02 |
| 4,888,998 A * | 12/1989 | Buzza et al. | ............. | 73/864.21 |
| 5,192,438 A * | 3/1993 | Frejborg | ..................... | 210/413 |
| 5,686,656 A * | 11/1997 | Amirav et al. | ............. | 73/23.41 |
| 5,775,972 A * | 7/1998 | Siu | ............................. | 446/468 |
| 6,293,162 B1 * | 9/2001 | Mathur et al. | ............ | 73/864.22 |
| 7,363,801 B2 * | 4/2008 | Tsuchihashi et al. | ....... | 73/23.41 |
| 2007/0137314 A1 * | 6/2007 | Watson et al. | ................. | 73/863 |

\* cited by examiner

*Primary Examiner*—Robert R Raevis
(74) *Attorney, Agent, or Firm*—Suiter Swantz pc llo

(57) ABSTRACT

The present invention is directed to a pressurized fluid station. In an exemplary embodiment, the pressurized fluid station includes a vessel for receiving a sample probe. The vessel includes walls contoured to form a seal around the sample probe. Further, a delivery system is coupled to the vessel for delivery of a pressurized fluid to the sample probe while the sample probe is disposed within the vessel. In use, the formation of a seal around the sample probe and delivery of a pressurized fluid into the probe while such probe is disposed within the vessel allows for removal of sample blockage from the probe as well as high speed rinsing of the sample probe in between analyses.

6 Claims, 3 Drawing Sheets

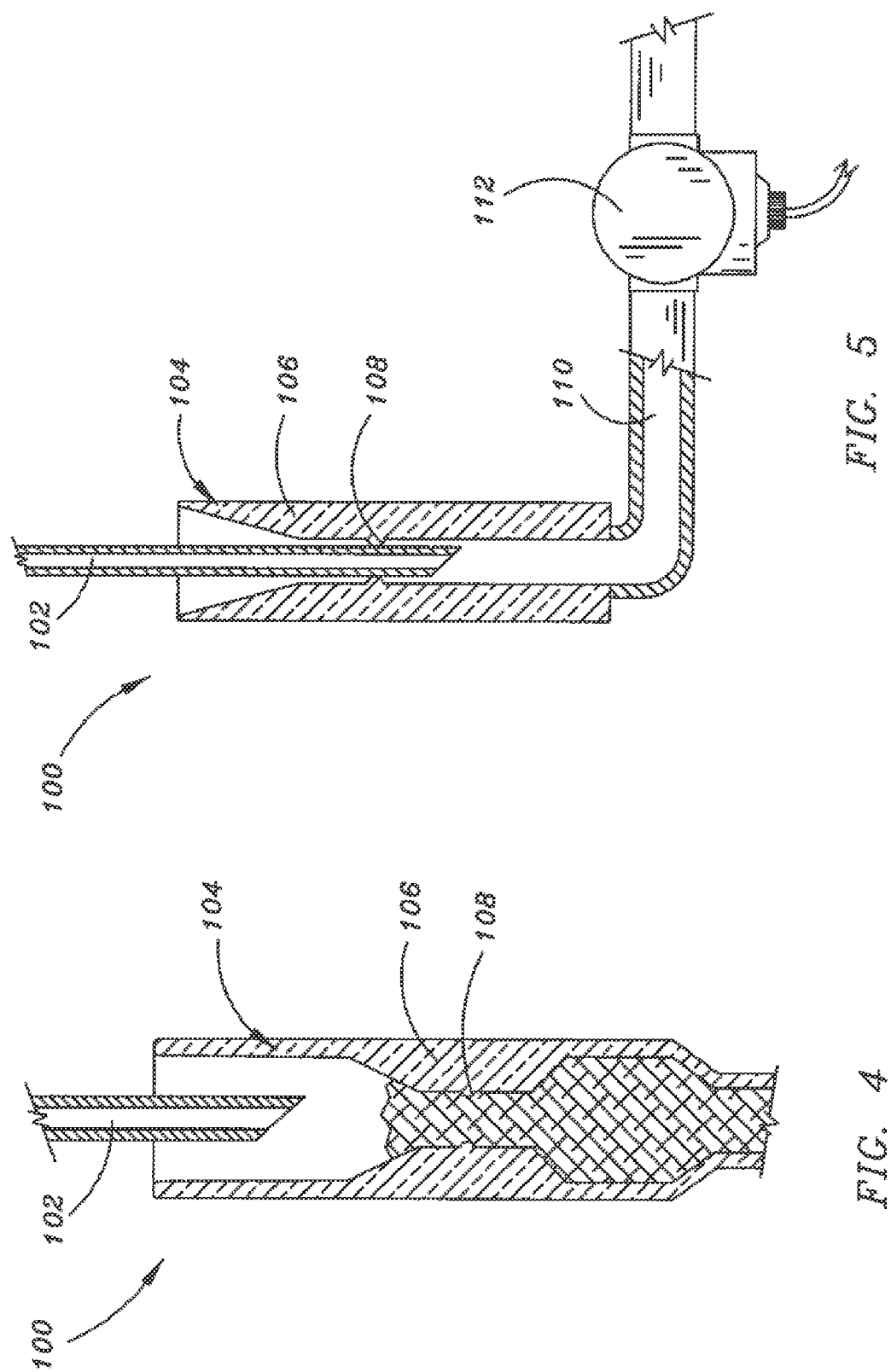

PRESSURIZED FLUID STATION

FIELD OF INVENTION

The present invention relates generally to laboratory instrumentation and particularly to a pressurized fluid station for removal of sample blockage or high speed rinsing of a sample probe.

BACKGROUND OF THE INVENTION

In many laboratory settings, it is often desired to convert liquid samples into aerosols prior to chemical analysis with a spectrometer or other analytical instrumentation. Such process is often performed by use of self-aspirating nebulizers. Self-aspirating nebulizers are advantageous in many regards the majority of which are associated with the elimination of a pumping system. First, the elimination of the use of a pumping system eliminates contamination associated with the use of such system. Further, the internal volume associated with the use of a pumping system often causing rinsing as well as sample loading time to be increased is eliminated. The problems related to pumping system contamination and internal volume are extremely significant when high purity samples are to be analyzed or when the volume of the sample is small, such as with biological samples, pre-concentrated samples or radioactive samples. In addition, periodic noise introduced into the analytical signal which adversely affects the detection limits and precision of the analytical measurement caused by the periodic motion of the pumping system is removed with the elimination of the pumping system.

Although self-aspirating nebulizers presently known in the art have greatly increased the ease of converting liquid samples to aerosols prior to chemical analysis, such instruments are still disadvantageous in many regards. One of the disadvantages of current self-aspirating nebulizers is flow stoppage caused by the presence of a plurality of gas bubbles or liquid/gas segments present in an uptake capillary. For example, each bubble causes a resistance to flow. If the sum resistance to flow is greater than the suction of the self-aspirating nebulizer, flow of liquid will cease. Bubble formation is a significant concern when utilizing conventional self-aspirating nebulizers with automated sampling systems. For instance, upon the leaving of a sample probe from a sample vessel containing liquid sample (e.g. a biological sample or viscous sample) a portion of the sample liquid adheres to the outer surface of the sample probe forming a film of liquid. As the sample probe travels to another location of the automatic sampling device, a portion of the adhering liquid film flows down the sample capillary and moves over the entrance to the sample capillary, where a segment of the film is taken up, causing the formation of a bubble in the sample capillary. The liquid film may then flow down across the opening of the sample capillary again, forming additional bubbles. Such phenomenon is illustrated in FIG. 3. Approximately ten to fifty bubbles may be introduced into a sample capillary which is sufficient to prevent the self-aspirating nebulizer from operating. User intervention is required to remove such bubbles and to return the self-aspirating nebulizer to operable condition. The need of periodic user intervention removes one of the major benefits associated with automated sampling devices whereby such systems may no longer be run unattended for the possibility of bubble formation leading to self-aspirating nebulizer inoperability.

To overcome flow stoppage, a user may employ a pumped nebulizer whereby a pump can generate several atmospheres of pressure to drive a sample into a nebulizer even in the presence of bubbles or other restrictions. As such, a pumped nebulizer typically produces more reliable (although more contaminated and larger sample volumes) sample flow into the analyzing instrument when compared to conventional self-aspirating nebulizers.

An additional disadvantage associated with prior art self-aspirating nebulizers is the inability to rinse samples at high speeds between analyses. For instance, it is often desired to deliver a higher flow of rinsing liquid between samples to faster effect complete elimination of the previous sample from the instrument prior to the analysis of a subsequent sample. Conventional self-aspirating nebulizers are limited to aspirating fluid at one rate or at very narrow ranges of flow rates. By comparison, a pumping system may operate at a variety of flow rates whereby flow rate is increased by simply increasing pump speed which, in turn, creates a higher pressure in the rinse solution stream driving the rinse solution to the nebulizer at a higher speed.

Thus, a user is presently required to choose between a pumped nebulizer which introduces contamination, pulsation, and additional volume into samples or employ a self-aspirating nebulizer which is plagued by unreliable sample flow and limitations on sample rinsing which requires periodic user intervention obviating the use of an automatic sampling system with unattended runs.

Therefore, it would be desirable to design a system which allowed a self-aspirating nebulizer to be utilized with an automated sampling device whereby the present limitations associated with conventional self-aspirating nebulizer of flow stoppage and inability to significantly alter flow rates were eliminated.

SUMMARY OF INVENTION

Accordingly, the present invention is directed to a pressurized fluid station. As such, the pressurized fluid station may be coupled to an automated sampling device allowing for removal of sample blockage from the automated sampling device sample probe as well as high speed rinsing of the sample probe in between analyses.

In accordance with a first aspect of the present invention, a pressurized fluid station is disclosed. In an exemplary embodiment, the pressurized fluid station includes a vessel for receiving a sample probe. The vessel includes walls contoured to form a seal around the sample probe. Further, a delivery system is coupled to the vessel for delivery of a pressurized fluid to the sample probe while the sample probe is disposed within the vessel. For instance, the pressurized fluid may be gas (e.g. argon, nitrogen, and atmospheric air) or a liquid. Further, in additional embodiments, the pressurized fluid station may be constantly pressurized or such fluid may be employed to increase the flow of a rinsing solution above the rate that would normally be self-aspirated. Moreover, a valve system for regulating the flow of the pressurized fluid to the pressurized fluid station may be included. In use, the formation of a seal around the sample probe and delivery of a pressurized fluid into the probe while such probe is disposed within the vessel allows for removal of sample blockage from the probe and the ability to rinse the sample probe at high speeds between analyses.

In accordance with a second aspect of the present invention, an automated sampling device with a pressurized fluid station is disclosed. In an exemplary embodiment, such device includes a sample probe. Further, the pressurized fluid station disposed within the automated sampling device for removal of blockages from the sample probe, includes a vessel for receiving a sample probe. The vessel includes walls contoured to form a seal around the sample probe. In addition, a delivery system is coupled to the vessel for delivery of a pressurized fluid to the sample probe while the sample probe is disposed within the vessel. For example, the pressurized fluid may be gas (e.g. argon, nitrogen, and atmospheric air) or a liquid. Furthermore, in additional embodiments, the pressurized fluid station may be constantly pressurized or such pressure may be employed to increase the flow of a rinsing solution above the rate that would normally be self-aspirated. Moreover, a valve system for regulating the flow of the pressurized fluid to the pressurized fluid station may be included. The arrangement of the automated sampling device with the pressurized fluid station allows for removal of sample blockage from the automated sampling device sample probe the ability to rinse the sample probe at high speeds between analyses.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles of the invention.

BRIEF DESCRIPTION OF DRAWINGS

The numerous objects and advantages of the present invention may be better understood by those skilled in the art by reference to the accompanying figures in which:

FIG. 4 is cross-sectional view of a pressurized fluid station in accordance with the present invention;

FIG. 5 is a cross-sectional view of a pressurized fluid station in accordance with the present invention, wherein a seal is formed around the sample probe and a delivery system including a valve is present for the delivery of pressurized fluid into the sample probe.

DETAILED DESCRIPTION OF INVENTION

Reference will now be made in detail to the presently preferred embodiments of the invention, examples of which are illustrated in the accompanying drawings.

Figure 1:
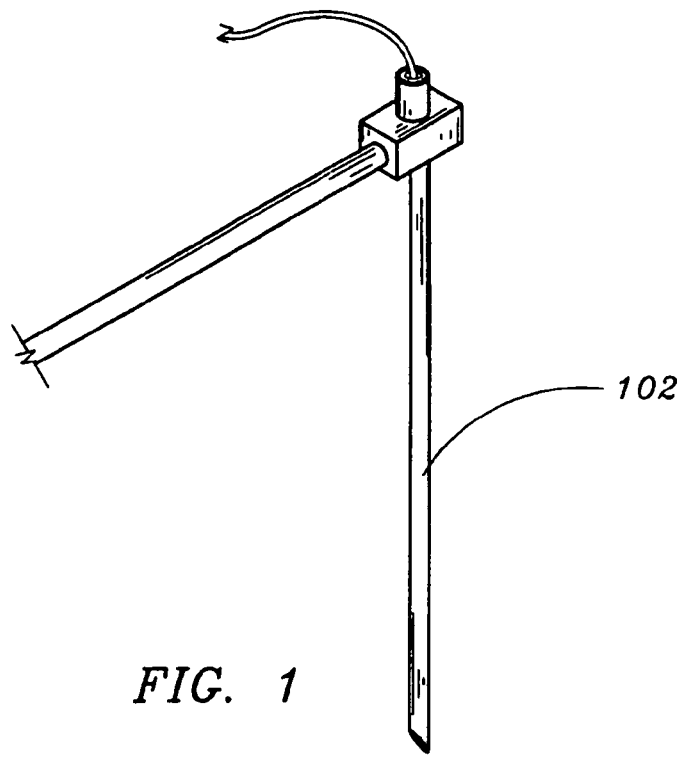
FIGS. 1, 2 and 3 are illustrations of a conventional sample probe demonstrating the typical problem of sample liquid adhesion and bubble formation encountered with the use of a conventional sample probe and a self-aspirating nebulizer.
Figure 2:
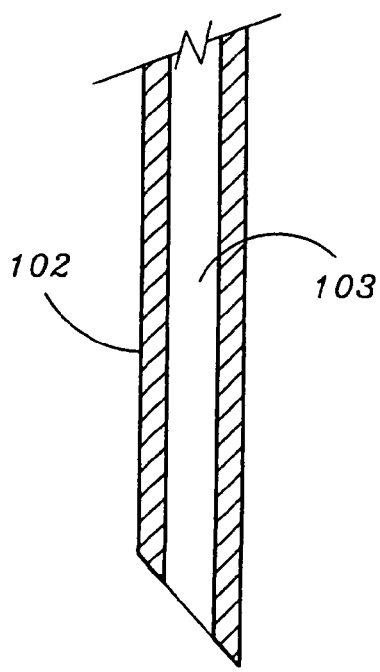
Figure 3:
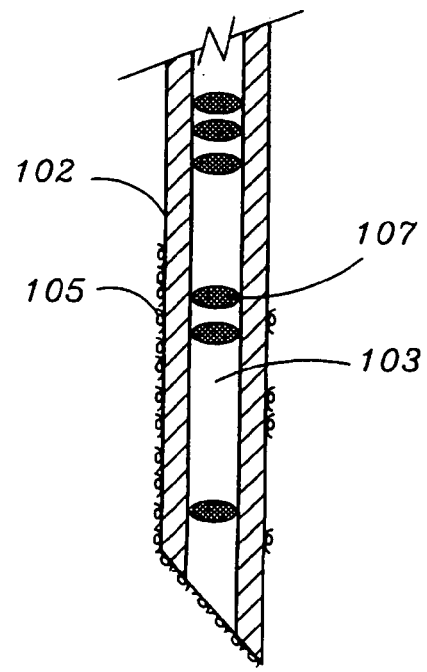

FIGS. 1, 2 and 3 are illustrations of a conventional sample probe demonstrating the typical problem of sample liquid adhesion and bubble formation encountered with the use of a conventional sample probe and a self-aspirating nebulizer. In particular, FIG. 1 is a depiction of a conventional sample probe 102 which is included within a sample arm assembly. FIG. 2 is an exploded view of such sample probe 102 wherein the internal capillary 103 within the sample probe may be viewed. FIG. 3 illustrates the problem which is typically encountered when using such sample probe 102 whereby upon the leaving of a sample probe 102 from a sample vessel containing liquid sample (e.g. a biological sample or viscous sample) a portion of the sample liquid adheres to the outer surface of the sample probe 102 forming a film of liquid 105. Further, as the sample probe 102 travels to another location of the automatic sampling device, a portion of the adhering liquid film 105 flows down the sample probe 102 and moves over the entrance to the internal sample probe capillary 103. As such, a segment of the film 105 is taken up, causing the formation of a bubble 107 in the internal capillary 103. The liquid film 105 may then flow down across the opening of the sample capillary 103 again, forming additional bubbles. Approximately ten to fifty bubbles may be introduced into the internal sample probe capillary 103 which is sufficient to prevent the self-aspirating nebulizer from operating. User intervention is required to remove such bubbles and to return the self-aspirating nebulizer to operable condition. Thus, the need for periodic user intervention removes one of the major benefits associated with automated sampling devices whereby such systems may no longer be run unattended for the possibility of bubble formation leading to self-aspirating nebulizer inoperability.

FIGS. 4 and 5 illustrate a pressurized fluid station 100 in accordance with the present invention. The use of the pressurized fluid station 100 allows a pressurized fluid to be delivered into the probe pushing bubbles, viscous samples, or other blockages from the probe thereby overcoming the disadvantages previously associated with the use of self-aspirating nebulizers with automated sampling systems.

In an exemplary embodiment, the pressurized fluid station 100 includes a vessel 104 for receiving a sample probe 102. The vessel 104 includes walls 106 contoured to form a seal 108 around the sample probe 102. In an advantageous embodiment, the inner contoured vessel walls 106 which make contact with the sample probe 102 are made from inert or fluoropolymer-covered materials (i.e. Teflon® PFA). For instance, Teflon® PFA (perfluoroalkoxy) is a desirable material due to the outstanding antistick properties as well as strong resistance to stress cracking and attack by nearly all chemicals and solvents that such material possesses. It should be understood, however, that such walls 106 may be made with any suitable material known in the art, including aluminum, steel, plastic, and the like. In an exemplary embodiment, an o-ring comprised of elastomer is used for the sealing element 108. In an advantageous embodiment, an o-ring with a flexible elastomeric core (e.g. silicon) surrounded by a fluoropolymer (e.g. Teflon® PFA) coating comprises the sealing element 108. Use of a fluoropolymer coated o-ring imparts greater chemical and temperature stability to such o-ring when compared to the conventional o-ring. In an alternative embodiment, an o-ring free seal is employed.

In the present embodiment, as illustrated in FIG. 5, a delivery system 110 is coupled to the vessel 104 for the delivery of a pressurized fluid to the sample probe 102 while the sample probe 102 is disposed within the vessel 104. It is contemplated that the delivery system 110 may include tubing flexible or rigid, comprised of plastic, metal, and the like. It is further contemplated that the pressurized fluid may be gas (e.g. argon, nitrogen, and atmospheric air) or a liquid. In additional embodiments, the pressurized fluid station 100 may be constantly pressurized or may be employed to increase the flow of a rinsing solution above the rate that would normally be self-aspirated. Moreover, a valve system 112 for regulating the flow of the pressurized fluid to the pressurized fluid station may be included within the delivery system 110. For instance, the valve system 112 may be configured to turn off the flow of the pressurized fluid when such fluid is not needed.

In an exemplary use, the sample probe 102 (which may be part of a sampling arm assembly of an automated sampling device) is inserted into the pressurized fluid station 100. Upon insertion, a seal is formed around the sample probe 102. Pressurized fluid, whether it be a liquid or a gas, is then delivered to the sample probe 102 via the delivery system 110.

In this embodiment, such fluid is delivered at a flow rate sufficient to push bubbles, viscous samples, or other blockages from the probe 102.

Figure 6:
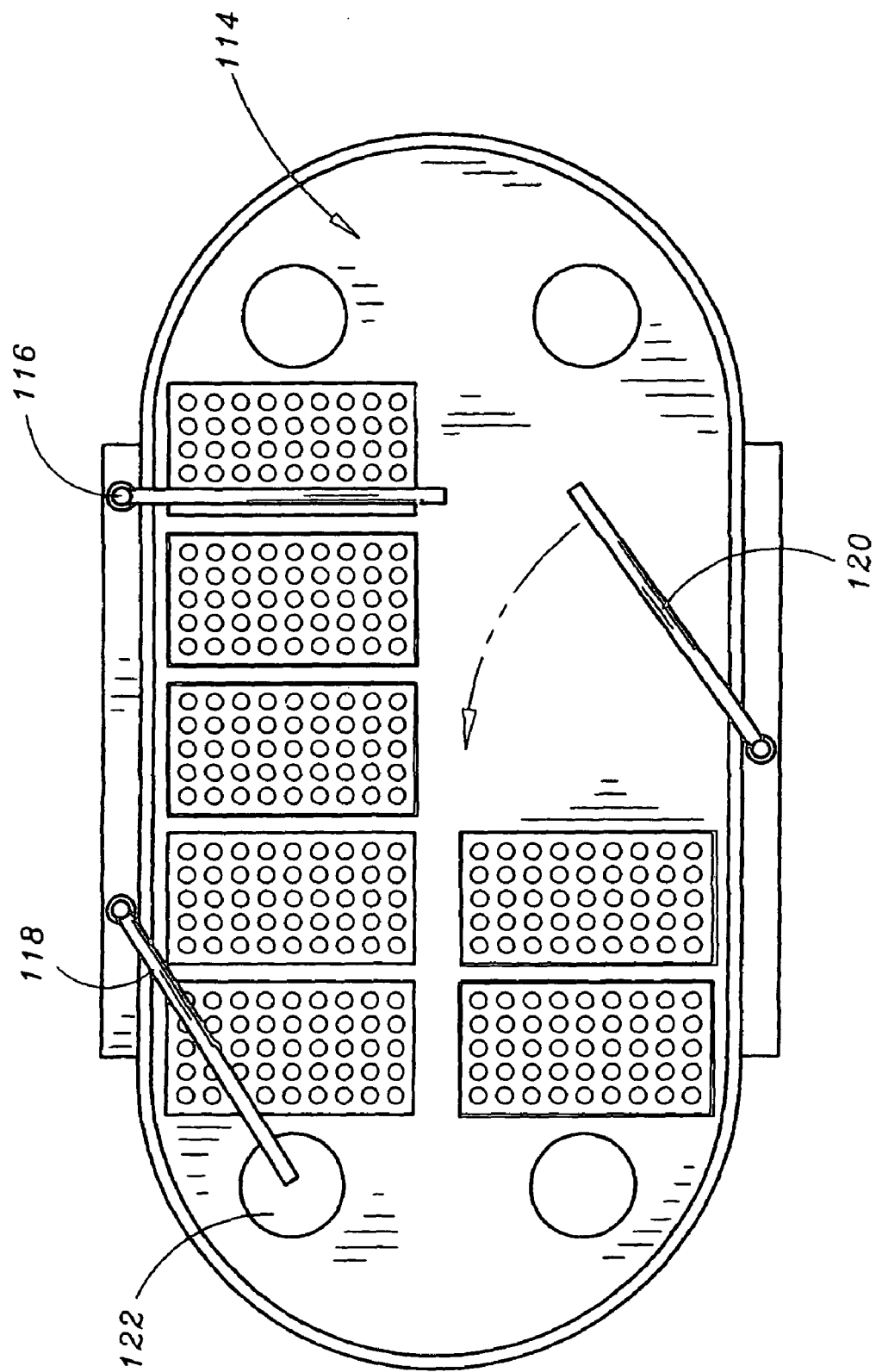
FIG. 6 is a top view illustrating a pressurized fluid station in accordance with a second exemplary embodiment of the present invention, wherein the pressurized fluid station is mounted within an automated sampling device.

FIG. 6 illustrates an additional embodiment of the present invention in which the pressurized fluid station 100 is contemplated to be disposed within a rinsing station of an automated sampling system 114. In the embodiment illustrated, the automated sampling device 114 includes multiple sample arm assemblies 116, 118, and 120 each of which include sample probes as illustrated previously (see FIGS. 1-5). Utilization of multiple sample arm assemblies allows multiple sample zones as illustrated by the circle denoted as 122 to be set up within a single automated sampling system 114 (e.g. a prep zone, assaying zone, rinsing zone, and the like). For example, various types of multiple rinse or eluent stations may be included in the automated sampling system 114.

In one exemplary embodiment, it is contemplated that a pressurized fluid station 100 is incorporated into the rinse station 122 located within the automated sampling system 114. Such configuration allows for high speed rinses of the sample probe 102 in between analyses. As described above, the pressurized fluid station 100 includes a vessel 104 for receiving a sample probe 102. The vessel 104 includes walls 106 contoured to form a seal 108 around the sample probe 102. In addition, a delivery system 110 is coupled to the vessel 104 for delivery of a pressurized fluid to the sample probe 102 while the sample probe 102 is disposed within the vessel 104. For example, the pressurized fluid may be gas (e.g. argon, nitrogen, and atmospheric air) or a liquid. Further, such fluid is employed to increase the flow of the rinsing solution above the rate that would normally be self-aspirated. Moreover, a valve system 112 for regulating the flow of the pressurized fluid to the pressurized fluid station 100 may be included. Although the present embodiment includes the pressurized fluid station 100 within the rinse station 122 of the automated sampling device 114, it is contemplated that such location may be altered without departing from the scope and spirit of the present invention. Thus, the arrangement of the automated sampling device 114 with the pressurized fluid station 100 may not only allow for high speed rinses of the sample probe in between sample analyses, but for the removal of sample blockage from the automated sampling device sample probe.

It is believed that the present invention and many of its attendant advantages will be understood by the foregoing description. It is also believed that it will be apparent that various changes may be made in size, materials, shape, form, function, manner of operation, assembly and use of the components thereof without departing from the scope and spirit of the invention or without sacrificing all of its material advantages. The form herein before described being merely an explanatory embodiment thereof. Further, it is contemplated that the specific order or hierarchy of steps in the method can be rearranged while remaining within the scope and spirit of the present invention. It is the intention of the following claims to encompass and include such changes.

What is claimed is:

1. An automated sampling device incorporated within a rinse station, comprising:

an automated sampling device for assaying and processing samples, the automated sampling device including a sample probe, the automated sampling device including a plurality of sample arm assemblies, each of the plurality of sample arm assemblies including a sample probe a pressurized fluid station disposed within the automated sampling device for removal of blockages from at least one of the sample probes of the plurality of sample arm assemblies, the pressurized fluid station constantly pressurized to increase the flow of a rinsing solution above a self-aspiration rate, the pressurized fluid station including a vessel for receiving at least one of the sample probes of the plurality of sample arm assemblies, the vessel including inner contoured walls substantially narrowing from a wider top region to a narrower lower region, the narrower lower region forming a seal around the sample probe, the seal making contact with the sample probe, the seal having a diameter less than the diameter of the sample probe; and a delivery system coupled to the vessel configured to deliver a pressurized fluid to the sample probe while the sample probe is disposed within the vessel, wherein the arrangement of the automated sampling device with the pressurized fluid station allows for removal of sample blockage from the automated sampling device sample probe as well as high speed rinsing of the sample probe in between analyses.

2. The automated sampling device of claim 1, wherein the pressurized fluid is a gas.

3. The automated sampling device of claim 2, wherein the gas is selected from the group consisting of argon, nitrogen, and atmospheric air.

4. The automated sampling device of claim 1, wherein the pressurized fluid is a liquid.

5. The automated sampling device of claim 1, further comprising a valve system for regulating the flow of the pressurized fluid to the pressurized fluid station.

6. The automated sampling device of claim 1, wherein the seal is formed of fluoropolymer material.

* * * * *